United States Patent [19]

Williams

[11] Patent Number: Plant 5,880

[45] Date of Patent: Feb. 17, 1987

[54] MINIATURE ROSE PLANT NAMED MINPCO

[76] Inventor: Ernest D. Williams, 1510 Lebanon Ave., Dallas, Tex. 75208

[21] Appl. No.: 728,666

[22] Filed: Apr. 29, 1985

[51] Int. Cl.[4] ..... A01H 5/00

[52] U.S. Cl. ..... Plt./7

[58] Field of Search ..... Plt./7, 9

*Primary Examiner*—Robert E. Bagwill

[57] ABSTRACT

The subject of the present disclosure is a new and distinct variety of miniature rose plant characterized by the pink and yellow color blend of the double flowers and by the profusion of bloom:

1 Drawing Figure

1

The present invention relates to a new and distinct variety of hardy, dwarf, bush type rose plant of the miniature class; the variety being primarily characterized—as to novelty—by the pink and yellow coloration of the buds and flowers which in general color effect are similar to Little Darling (a floribunda—U.S. Pat. No. P.P. 1,581, expired), but smaller in size.

The variety is further characterized by:

An abundance of bloom, with flowers usually borne singly.

Slight fragrance.

A plant which is vigorous, of bushy, growth habit with semi-glossy to glossy, small foliage with pointed leaflets; the buds and flowers being similar in form to Over The Rainbow (miniature—U.S. Pat. No. P.P. 3,472) and averaging more petals.

The plant, which has a normal height of about 30 cm or more, can easily be maintained at lesser height by occasional trimming.

A plant which grows and blooms satisfactorily outdoors; is good for growing in pots; and provides excellent garden decoration as well as cut flowers.

The present variety of miniature rose was originated by me at my nursery located at Dallas, Tex., under conditions of careful control and observation, as a cross between Little Darling (a floribunda—U.S. Pat. No. P.P. 1,581, expired) as the seed parent and Over The Rainbow (miniature—U.S. Pat. No. P.P. 3,472) as the pollen parent.

Subsequent to origination of the variety I successfully reproduced it, at my nursery located as aforesaid, by cuttings; the reproductions having run true in all respects.

The color photograph illustrates the variety, including the foliage, bud and flower.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy; dwarf; bushy; slightly spreading; seedling; outdoors; cut flowers; garden decoration; potted plant.

Class: Miniature.

*Variety identification.*—Minpco.

*Commercial synonym.*—Partyglo.

Flowers borne: Usually singly on slender wirey stems.

Quantity of bloom: Abundant.

2

Bud:

*Peduncle.*—Medium to long length; slender but sturdy; erect; medium green, sometimes tinted bronze (outdoors); hairs — few to none.

*Before calyx breaks.*—Size — small. Form long; pointed with few or no foliaceous apendages and few or no tiny hairs on surface of bud; with foliaceous parts extending beyond the tip of the bud equal to one-half or less of its length. Color — medium green, occasionally tinted with bronze (outdoors).

*As calyx breaks.*—Color — yellow.

*Opening.*—Opens well in all weather.

Bloom:

*Size, when fully open.*—Small, averaging about 35–40 mm (1½").

*Petalage.*—Double — averaging about 26–40 petals, arranged regularly plus sometimes several small petaloids.

*Form.*—High centered with petals reflexing loosely outward and later, at maturity, rolled loosely outward and downward. Open flower show stamens.

Petals: Fairly thick; satiny on inside and on outside surface.

*Shape.*—Outside petals, broad lanceolate; intermediate — broad lanceolate with acute tip; inside — lanceolate with acute tip.

Color: Newly opened flower from a plant grown outdoors; (1984 season), Dallas, Tex.

*Outside petal.*—Outside surface — soft yellow blending into soft pink. Inside surface — near Azalea Pink 618/3 blending (or shading) into a color similar to Azalea Pink 618/2 (or darker) near petal tips.

*Intermediate petal.*—Outside surface — same as outside petal; inside surface — similar to outside petal.

*Inner petal.*—Outside surface — same as intermediate petal. General color effect; newly opened flowers — bright deep pink. Three days open — color similar to newly opened flowers but less brilliant. Behavior — opens well in all weather. Flower longevity (May 1984) — plant in pot 6–8 days or longer. Cut flowers at living room temperature 4–5 days or longer.

Reproductive organs:

*Stamens.*—Average.

*Filaments.*—Generally long, yellow.

*Anthers.*—Yellow.

*Pollen.*—Fairly abundant — yellow.

*Pistils.*—Average number.

*Styles.*—Fairly even; medium length; bunched; color — yellowish.

*Ovaries.*—All enclosed in calyx.

*Hips.*—Few to none.

*Sepals.*—Permanent; spear shaped; recurved against peduncle.

*Seed.*—Few to none.

Foliage:

*Leaves.*—Compound of five (sometimes three or seven) leaflets; fairly small; leathery; semi-glossy to glossy.

*Leaflets.*—Shape: broad lanceolate, apex acute; base rounded, or rounded acute. Margin serrate.

*Color.*—Medium to dark green; new growth — normal (medium) green — sometimes tinted bronze.

*Rachis.*—Medium strength; upper side may have several tiny short prickles or hairs, grooved; underside several short to medium length hooked thorns with few or no tiny prickles.

*Stipules.*—Medium long; medium width; long; narrow points which turn out usually at about 45 degrees or less.

Growth:

*Habit.*—Dwarf; bushy; upright to slightly spreading; much branched.

*Growth.*—Free, vigorous; internodes short.

*Canes.*—Medium; slender; sturdy.

*Main stems.*—Color: medium green.

*Thorns.*—Average; slender, hooked slightly downward; color; tan. Prickles — none. Hairs — none.

*Branched.*—Color: medium green. Thorns: average to numerous; medium to long; slender; nearly straight, inclined downward. Medium oval base. Prickles: none. Hairs: none.

The miniature rose plant and its flowers as herein described may vary in slight detail due to climatic, soil and cultural conditions under which the variety may be grown; the present description being of the variety as grown at Dallas, Tex.

The following is claimed:

1. A new and distinct variety of miniature rose plant of hardy, dwarf, bushy, upright to slightly spreading, much branched habit substantially as illustrated and described, characterized by buds and flowers of a soft to medium pink color, being of a shade generally near Azalea Pink 618/3 or deeper, the bud and flower resembling the variety Over The Rainbow (U.S. Pat. No. P.P. 3,472) in form, and Little Darling in color (but smaller in size); and further characterized by a plant of vigorous and compact growth habit, easy to propagate from cuttings, with an abundance of flowers borne usually one to the stem.

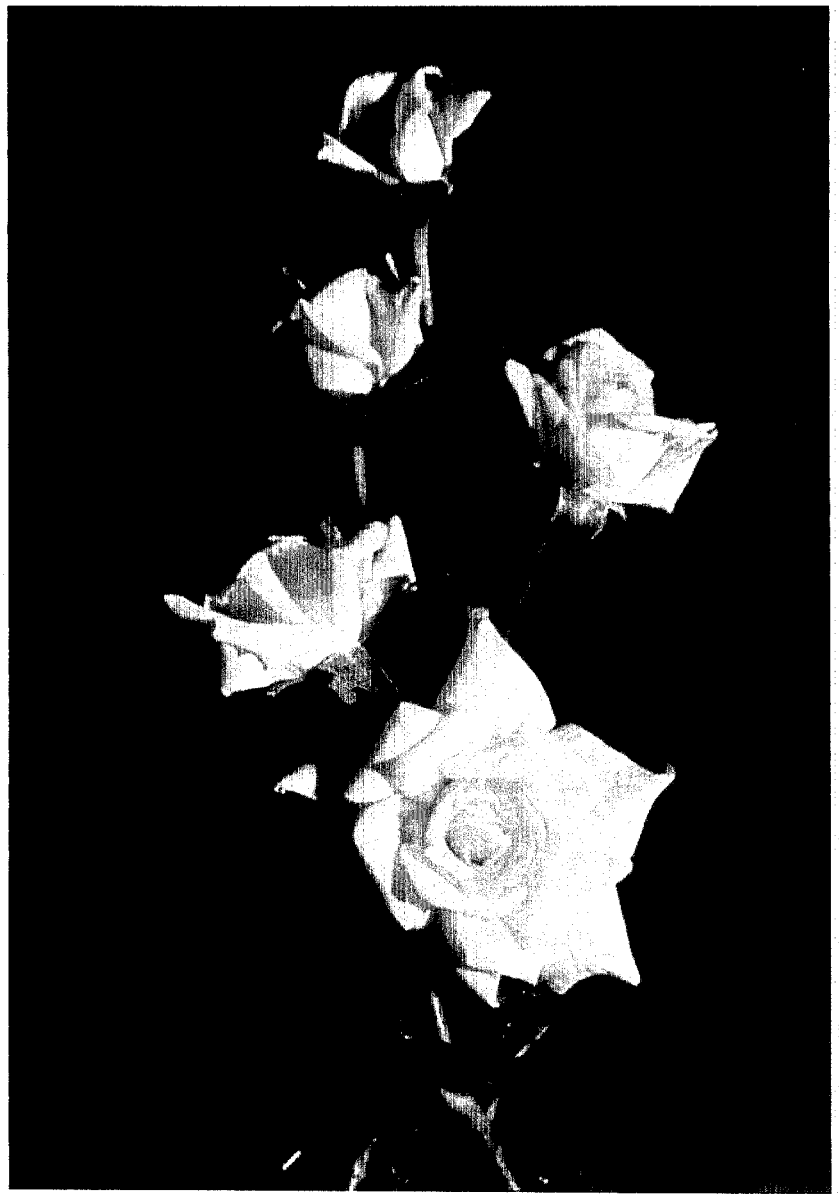

* * * * *